United States Patent [19]

Burns et al.

[11] Patent Number: 4,994,258
[45] Date of Patent: Feb. 19, 1991

[54] GAMMA EMITTING, CCK-A ANTAGONISTS FOR PANCREATIC IMAGING

[75] Inventors: H. Donald Burns, Harleysville; Nancy J. Brenner, Macungie; Raymond E. Gibson, Holland; Howard F. Solomon, New Hope, all of Pa.

[73] Assignee: Merck & Co., Inc., Rahway, N.J.

[21] Appl. No.: 488,192

[22] Filed: Mar. 5, 1990

[51] Int. Cl.$^5$ .................... A61K 49/02; C07D 243/24
[52] U.S. Cl. ...................................... 424/1.1; 540/509
[58] Field of Search ........................ 540/509; 424/1.1

[56] References Cited

U.S. PATENT DOCUMENTS

| | | | |
|---|---|---|---|
| 4,528,177 | 7/1985 | Molloy et al. | 424/1.1 |
| 4,628,084 | 12/1986 | Bock et al. | 540/509 |
| 4,820,834 | 4/1989 | Evans et al. | 540/504 |

OTHER PUBLICATIONS

Yamamoto et al., *J. Nuclear Medicine,* 26, pp. 765–769 (1985).
Frost et al., *J. Nuclear Medicine,* 30, pp. 849–850, No. 503 (1989).
Burns et al., *J. Nuclear Medicine,* 30, p. 931, No. 858 (1989).

*Primary Examiner*—John S. Maples
*Attorney, Agent, or Firm*—Hesna J. Pfeiffer; Raymond M. Speer; William H. Nicholson

[57] ABSTRACT

Novel radiolabeled cholecystokinin-A (CCK-A) antagonists have been developed which, after intravenous injection, localize in the pancreas as a result of specific binding to CCK-A receptors. These tracers, when labeled with appropriate radiohalogens, are useful as commercial diagnostic imaging radiopharmaceuticals and radiotherapeutic drugs.

14 Claims, No Drawings

GAMMA EMITTING, CCK-A ANTAGONISTS FOR PANCREATIC IMAGING

BACKGROUND OF THE INVENTION

Noninvasive, nuclear imaging techniques can be used to obtain basic and diagnostic information about the physiology and biochemistry of a variety of living subjects including experimental animals, normal humans, and patients. These techniques rely on the use of sophisticated imaging instrumentation which is capable of detecting radiation emitted from radiotracers administered to such living subjects. The information obtained can be reconstructed to provide planar and tomographic images which reveal the distribution of the radiotracer as a function of time. Use of appropriately designed radiotracers can result in images which contain information on structure (low resolution), function, and most importantly, physiology and biochemistry of the subject. Much of this information cannot be obtained by any other means. The radiotracers used in these studies are designed to have defined behaviors in vivo which permit the determination of specific information concerning the physiology or biochemistry of the subject or of the effect that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose, and oxygen metabolism. A major effort has been made over the past 30 years to develop radiotracers to image the pancreas with little success (see Tothill, p., Heading, R.C., Shearman, D.J.C. In: *Radiopharmaceuticals and Labelled Compounds*, proceedings of a symposium, Copenhagen, March 1973, 1:26–30).

A variety of radiotracers have been proposed for pancreatic imaging including compounds labeled with either positron or gamma emitting nuclides. For imaging, the most commonly used positron emitting radiotracers are $^{11}C$, $^{18}F$, $^{15}O$, and $^{13}N$, all of which are accelerator produced, and have half-lives of 20, 110, 10, and 2 min respectively. Since the half-lives of these radionuclides are so short, it is only feasible to use them at institutions which have an accelerator on site for their production, limiting their use to approximately 25 medical centers in the U.S. and only about 50 throughout the world. Several gamma emitting radiotracers are available which can be used by essentially any hospital in the U.S. and in most hospitals throughout the world. The most widely used of these are $^{99m}Tc$, $^{201}Tl$, and $^{123}I$. $^{201}Tl$ is a monovalent cation which is used for measuring myocardial blood flow. Both $^{99m}Tc$ and $^{123}I$ can be incorporated into a variety of radiotracers and are widely used in most modern hospitals. $^{99m}Tc$ is generator produced, has a 6 hour half life, and emits a 140 keV gamma photon which makes this radionuclide photon emission computerized tomography (SPECT) cameras. $^{99m}Tc$ is a transition metal which forms a wide variety of complexes with molecules containing coordinating ligands (e.g. molecules with free thiol, amine, carboxyl functional groups). $^{99m}Tc$ labeled compounds have been developed for many diagnostic imaging applications, such as functional studies (e g. cardiac, renal, liver) and perfusion studies (myocardial, brain, lung). The design of these tracers is complicated and not relevant to the present invention.

$^{123}I$ is also nearly ideal for use with planar and SPECT cameras. It is accelerator produced, has a 13 hour half-life, and emits a 159 keV gamma photon which is efficiently detected by both planar and SPECT cameras. The most important advantage $^{123}I$ has as a radiotracer for imaging applications is its ability to form covalent bonds with carbon which, in many cases, are stable in vivo and which have well understood effects on physiochemical properties of small molecules.

In the past few years, one of the most active areas of nuclear medicine research has been in the development of receptor imaging radiotracers. These tracers bind with high affinity and specificity to selective hormone and neuroreceptors. Successful examples include radiotracers for imaging the following receptors: estrogen, muscarinic, dopamine D1 and D2, and opiate. These tracers are useful for obtaining information on receptor distribution and concentration as well as on regional blood flow. Most of this work has focused on positron emitting radiotracers. However, $^{123}I$ has been used to label small molecules to yield several radiotracers useful for receptor imaging; successful examples include 3 iodoquinuclidinyl benzilate and iodo-dexetimide for muscarinic receptors, iodo estradiol for estrogen receptors, and (S)-3-([$^{125}I$]-iodo-N-[(1-ethyl-2-pyrrolidinyl)-]methyl-2-hydroxy-6-methoxybenzamide for dopamine-D2 receptors.

Pancreatic Imaging:

Cancer of the pancreas is hard to diagnose at a stage when it is treatable. The location of the pancreas makes it difficult to examine. It is obscured by other organs of comparable density, principally the liver, and can be visualized radiographically only in extreme cases of calcification. Development of a suitable radiotracer for pancreatic imaging has been an elusive goal of many nuclear medicine researchers. Attempts to develop radiotracers to image the pancreas have been largely unsuccessful. Currently, the only tracer commercially available for pancreatic imaging is $^{75}Se$-selenomethionine which is of limited use, primarily due to the poor physical characteristics of $^{75}Se$ for imaging applications. Only 5–7% of this tracer localizes in the pancreas, and there is high uptake in adjacent organs, primarily the liver. The long half-life (120 days) and slow biological clearance of this high energy emitter limits the size of the administered dose. Furthermore, image resolution is complicated by the complex gamma spectrum of $^{75}Se$ [121 (17%), 136 (57%), 265 (60%), 280 (25%), 401 (12%) keV]. A clear need exists for a better pancreatic imaging radiotracer.

A wide variety of radiotracers have been evaluated as potential pancreatic imaging agents, including compounds labeled with both positron and gamma emitting radionuclides. For reviews on this subject, see Risch, V. Chapter 4, In: *The Chemistry of Radiopharmaceuticals*, N. D. Heindel, H. D. Burns, T Honda, L. W. Brady, eds., Masson, N.Y., 53–73, 1978; Fankuchen, E.I., Surg. Clin. North Am., 61:17–45, 1981; and Gross, M.D., Shapiro, B., Thrall, J. H., Freitas, J.E., Beierwaltes, W.H., *Endocrine Reviews* 5:221–281, 1984. Although many compounds have been evaluated for pancreatic imaging, none have offered significant improvement over $^{75}Se$-seleno-methionine. Recently, however, promising results have been reported for [$^{131}I$]N, N, N'-trimethyl-N'-(2-hydroxy-3-methyl-5-iodobenzyl)-1, 3-propanediamine, [$^{131}I$]HIPDM (Yamamoto, K. Som, P., Srivasteva, S.C., Meinken, G.E., Brill, A.B., *J. Nucl.*

Med. 26:765-769, 1985). Studies of this tracer in mice show that HIPDM localizes in the pancreas and suggest that this tracer may be useful for pancreatic imaging.

Cholecystokinin, CCK is a gastrointestinal, peptide hormone which has a direct effect on the pancreas, binding to specific CCK receptors and stimulating the release of pancreatic digestive enzymes. N-(2,3 Dihydro-1-methyl-2-oxo-5-phenyl-1H-1,4-benzodiazepine-3-yl) -1H-indole-2-carboxamide,

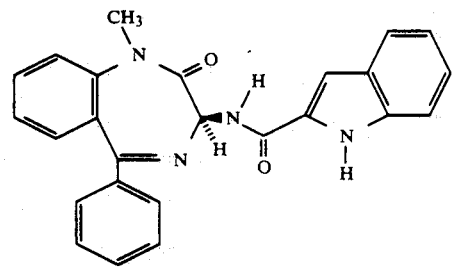

is a potent, nonpeptidal CCK-A antagonist which binds with high affinity ($K_i = 0.1$ nM) to CCK-A receptors. CCK-A is a subtype of CCK receptors which is found predominantly in the pancreas and muscle of the gallbladder, but is also found sparingly in the CNS, primarily in the solitary tract and substantia gelatenosa in man.

As used herein, the term "agonist" denotes ability to initiate or promote a particular drug activity. The term "antagonist" denotes the ability to block a particular drug activity.

N-(2,3-dihydro-1-methyl-2-oxo-5-phenyl-1H-1,4-benzodiazepine-3-yl) -1H-indole-2-carboxamide has been labeled with tritium and with $^{11}C$. Since tritium is a low energy beta emitter, it is not useful for noninvasive imaging. $^{11}C$ is suitable for noninvasive imaging, but because of its short half-life, it is not widely available. Biodistribution studies in mice with both $^3H$ and $^{11}C$ labeled N-(2,3-dihydro-1-methyl-2-oxo-5-phenyl-1H-1,4-benzodiazepine-3-yl) -1H-indole-2-carboxamide have demonstrated that, at high specific activity, the compound localizes in the pancreas (76% dose/gram at 4 hours post intravenous injection) and that this localization is blockable with high doses of the unlabeled compound. Thus, these studies indicate that the pancreatic localization is due to selective binding of N-(2,3-dihydro-1-methyl-2-oxo-5-phenyl-1H-1,4 benzodiazepine-3-yl) -1H-indole-2-carboxamide to CCK-A receptors. These results indicate that a suitable radiolabeled analog of N-(2,3-dihydro-1-methyl-2-oxo-5-phenyl -1H-1,4-benzodiazepine-3-yl)-1H-indole-2-carboxamide, which binds with high affinity to CCK-A receptors, would be useful for pancreatic imaging, and with appropriate radiolabels, may also be useful for radiotherapeutic treatment of pancreatic cancer. The most suitable radionuclide for imaging would be $^{123}I$, although other radiohalogens, including $^{122}I$, $^{125}I$, $^{131}I$, $^{77}Br$, $^{82}Br$, $^{211}At$, and $^{75}Br$, would also be useful for diagnostic imaging and therapeutic applications.

DETAILED DESCRIPTION OF THE INVENTION

The present invention is directed toward radiolabelled compounds of Formula I:

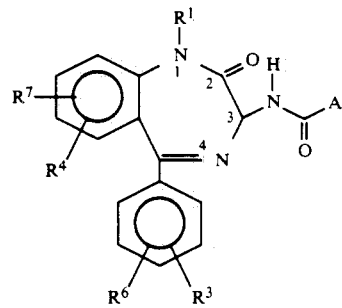

wherein:
A is

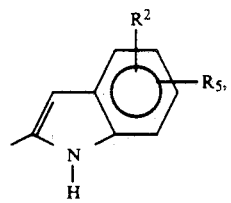

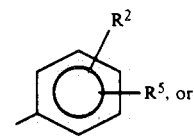

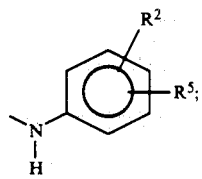

$R^1$ is H, $C_1$-$C_6$ linear or branched alkyl, $(CH_2)_nCOOR^8$, $(CH_2)_nOH$, $(CH_2)_nCN$, $(CH_2)_nNR^9R^{10}$,

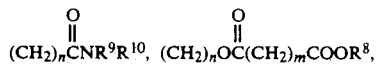

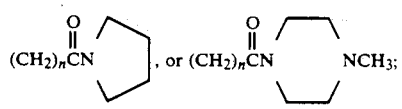

$R^2$ is H, —OH, —$NO_2$, F, Cl, $SO_3H$, loweralkyl, loweralkoxy, $(CH_2)_pCOOR^8$ or $(CH_2)_pNR^9R^{10}$;
$R^3$, is H, —OH, —$NO_2$, $CF_3$, F, Cl, loweralkyl, or loweralkoxy;
$R^4$ is H, —OH, —$NO_2$, $CF_3$, CN, F, Cl, loweralkyl, loweralkoxy, $(CH_2)_pCOOR^8$ or $(CH_2)_pNR^9R^{10}$;
$R^5$, $R^6$ and $R^7$ are, independently, H or a radionuclide selected from the group consisting of $^{122}I$, $^{123}I$, $^{125}I$, $^{131}I$, $^{75}Br$, $^{77}Br$, $^{82}Br$, $^{211}At$, with the proviso that at least one of $R^5$, $R^6$ and $R^7$ is not H;
$R^8$ is H or loweralkyl;
$R^9$ and $R^{10}$ are, independently, H or loweralkyl;

n is 1–4;

m is 1–2;

p is 0–4; or pharmaceutically acceptable salt thereof.

As used herein, the definition of each expression, e.g. m, n, p, loweralkyl, etc., when it occurs more than once in any structure, is intended to be independent of its definition elsewhere in the same structure.

In the compounds of the present invention, the components having asymmetric centers occur as racemates, racemic mixtures, and as individual diastereomers, with all isomeric forms generally being included in the present invention. In particular, the preferred stereochemistry for CCK-A antagonism relates to D-tryptophan, where C-2 and N 4 of Formula I correspond to the carbonyl carbon and α-amino nitrogen of D-tryptophan and —NHCOA occupies the position of the indolylmethyl side chain.

As used herein, loweralkyl is 1–7 carbon straight or branched chain alkyl and includes methyl, ethyl, propyl, isopropyl, n-butyl, isobutyl, t butyl, sec-butyl, pentyl, hexyl, and heptyl; in loweralkoxy, the alkyl portion is lower alkyl as previously defined.

The following additional abbreviations have also been used herein:

| Abbreviated Designation | Activating Group |
|---|---|
| NHS | N-hydroxysuccinimide |
| | Reagent |
| TFA | trifluoroacetic acid |
| Et₃N | triethylamine |
| CAT | (N-chloro-p-toluene-sulfonamido)sodium |
| DTT | dithiothreitol |
| | Solvent |
| HOAc (AcOH) | acetic acid |
| CH₂Cl₂ | dichloromethane |
| DMF | dimethylformamide |
| DMSO | dimethyl sulfoxide |
| EtOAc | ethyl acetate |
| EtOH | ethanol |
| Et₂O | ether |
| MeOH | methanol |
| THF | tetrahydrofuran |
| | Buffer |
| BSA | bovine serum albumin |
| PBS | phosphate buffered saline |
| Tris | Tris(hydroxymethyl)-aminomethane |

The pharmaceutically acceptable salts of the compounds of Formula I include the conventional non-toxic salts or the quarternary ammonium salts of the compounds of Formula I formed, e.g., from non-toxic inorganic or organic acids or bases. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or quaternary ammonium hydroxide such as tetramethylammonium hydroxide and the like.

The compounds of the present invention bind with high affinity and selectivity to CCK-A receptors which are found in high concentration in the pancreas and gallbladder. As a result of this binding to CCK A receptors, these tracers localize selectively in the pancreas after intravenous injection. For this application, these radiotracers must have a high affinity ($K_i < 10$ nM) for the receptor and they must be labeled with a suitable radionuclide. Radiolabeled CCK-A antagonists are useful in receptor assays, in autoradiography, as diagnostic imaging agents and as radiotherapeutic drugs. Suitable radionuclides includes $^{122}$I, $^{123}$I, $^{125}$I, $^{131}$I, $^{75}$Br, $^{77}$Br, $^{82}$Br, and $^{211}$At. Specific applications for each radionuclide are shown in Table 1.

TABLE 1

| Radiohalogens Useful for Imaging and Therapeutic Applications | | |
|---|---|---|
| Nuclide | Half-life | Application |
| $^{122}$I | 3.6 min | Imaging |
| $^{123}$I | 13.3 hr | Imaging |
| $^{125}$I | 60.0 days | Autoradiography, Radioimmunoassay, Therapy |
| $^{131}$I | 8.0 days | Therapy, Imaging |
| $^{75}$Br | 1.6 hr | Imaging |
| $^{77}$Br | 56.0 hr | Imaging |
| $^{82}$Br | 35.5 hr | Research Applications |
| $^{211}$At | 7.2 hr | Therapy |

For the use of the compounds of the present invention as diagnostic imaging agents it is preferred that the radionuclide be $^{123}$I, $^{131}$I, $^{75}$Br or $^{77}$Br. For the use of the compounds of the present invention as basic research tools (in radioimmunoassays and autoradiography), it is preferred that the radionuclide be $^{125}$I or $^{82}$Br. For the use of the compounds of the present invention as radiotherapeutic drugs, it is preferred that the radionuclide be $^{125}$I, $^{131}$I or $^{211}$At.

Applications for Radiohalogenated CCK-A Antagonists:

Radiolabeled CCK-A antagonists, when labeled with an appropriate radiohalogen, are potentially commercially useful for diagnostic imaging, basic research, and radiotherapeutic applications. Specific examples of possible diagnostic imaging applications include:

1. Location of primary and metastatic tumors of the pancreas:
    exocrine tumors;
    adenocarcinoma;

cystadenocarcinomas;
endocrine tumors-insulinomas;
gastrinomas (intra- and extra-pancreatic sites);
vipoma;
extra-pancreatic sites);
multiple endocrine neoplasia;
(pancreatic components);
glucagonoma.
2. Diagnosis and staging of carcinoma of the gallbladder.
3. Diagnosis and staging of carcinoma of the extrahepatic ducts.
4. Differentiation between pancreatitis and neoplasia.
1 5. Diagnosis of pancreatic necrosis.
6. Diagnosis of pancreatic abscess.
7. Diagnosis of pancreatic pseudocyst.
8. Evaluation of malabsorption syndromes.
9. Evaluation of cystic fibrosis with respect to the pancreas.
10. Diagnosis of obstruction of the extrahepatic ducts.
11. Evaluation of disorders of gastrointestinal tract, for example: gastric emptying, irritable bowel syndrome, gastroesophageal reflux disorder
12. Morphine potentiation.

Specific examples of possible commercial applications in basic research include:
1. Radioimmunoassay of cholecystokinin-A anatagonists.
2. Radioimmunoassay to determine the concentration of cholecystokinin-A receptors in a tissue sample.
3. Autoradiography to determine the distribution of cholecystokinin-A receptors in a mammal or an organ or tissue sample thereof.

Specific examples of possible radiotherapeutic applications include:
1. Treatment of primary and metastatic tumor of the pancreas, including exocrine tumor.
2. Treatment of carcinoma of the gallbladder.
3. Treatment of carcinoma of the extraheptic ducts.

The compounds of Formula I thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including by intravenous and intraperitoneal administration.

For oral use of a radiohalogenated antagonist of CCK-A, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intraperitoneal and intravenous use, sterile solutions or microfine emulsions of the active ingredient are usually prepared, and the pH of the solutions should be suitably adjusted and buffered. For intravenous use, the total concentration of solutes should be controlled in order to render the preparation isotonic.

When a compound according to Formula I is used in a human subject, the amount required for diagnostic imaging will normally be determined by the prescribing physician with the amount generally varying according to the age, weight, and response of the individual patient, as well as the radiohalogen employed. However, in most instances, an effective amount will be in the range of from about 1-5 mCi. In some cases, however, it may be necessary to use amounts outside these limits.

The compounds of Formula I are prepared according to the following schemes wherein X, Y and Z are, independently, hydrogen, iodo, or bromo, with the proviso that at least one of X, Y or Z is not hydrogen, and $R^1$-$R^7$ are as defined above.

REACTION SCHEME 1

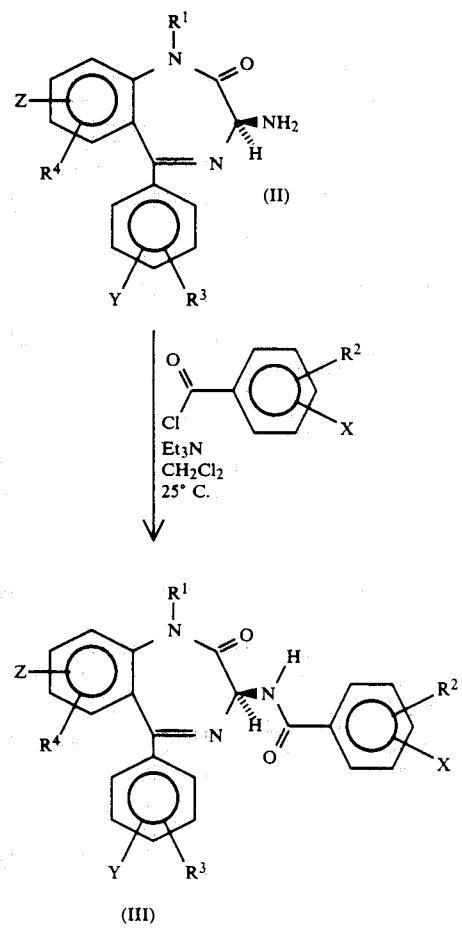

REACTION SCHEME 2
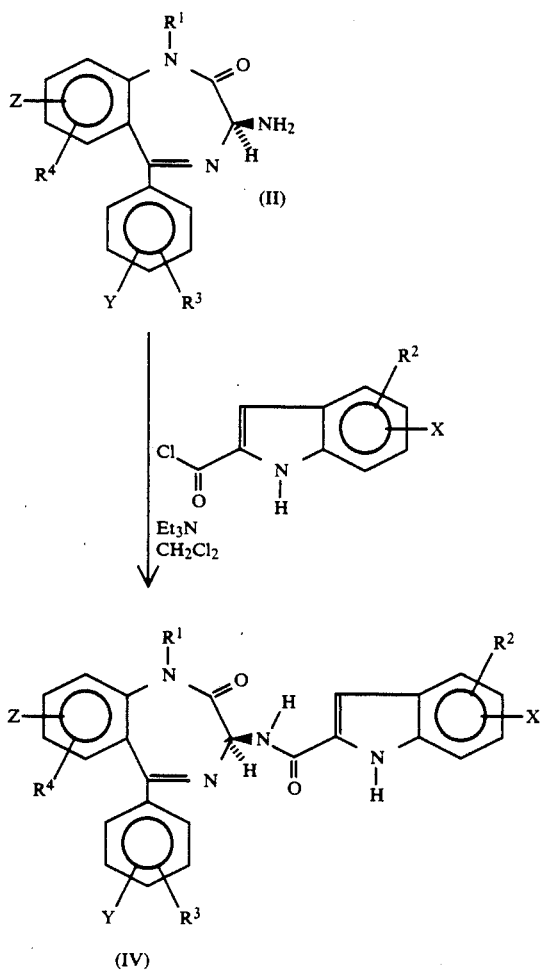
REACTION SCHEME 3
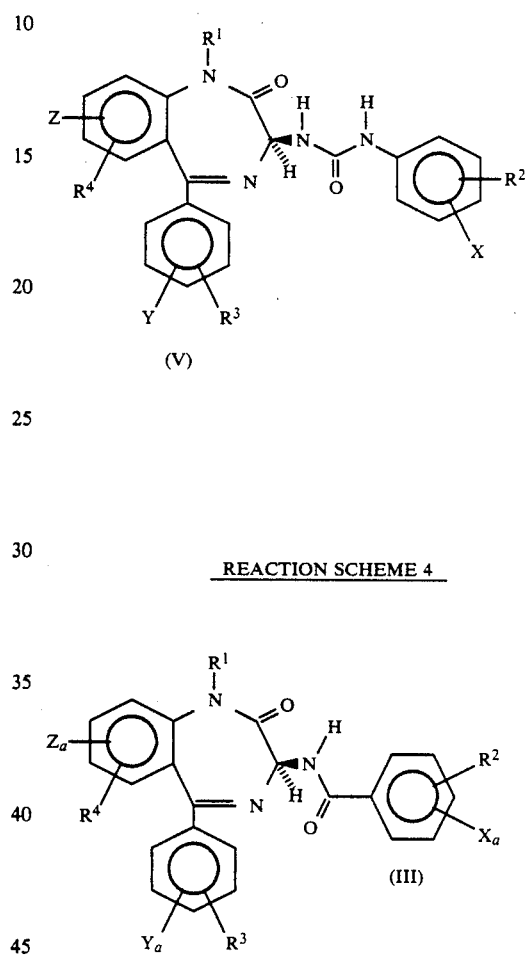
REACTION SCHEME 4
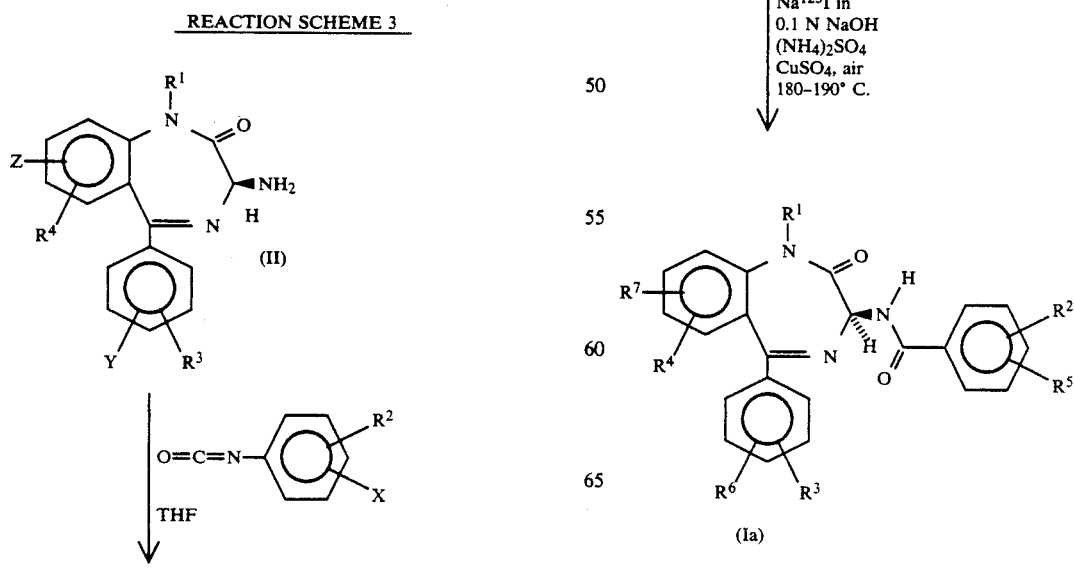

REACTION SCHEME 5

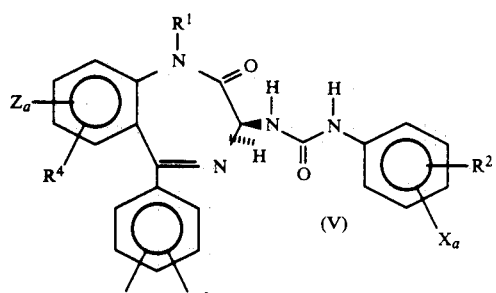

(V)

Na¹²³I in
0.1 N NaOH
(NH₄)₂SO₄
CuSO₄, air
180-190° C.

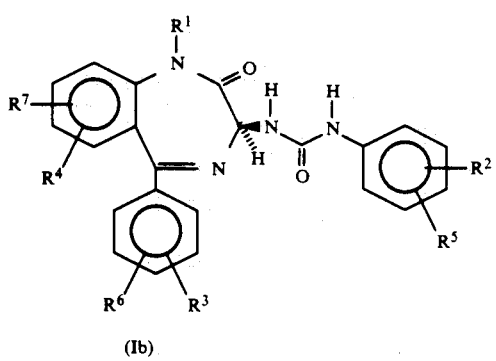

(Ib)

REACTION SCHEME 6

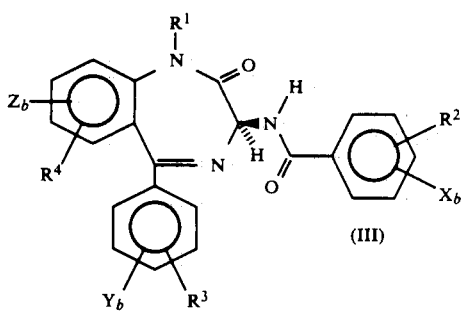

(III)

Na¹²³I
in 0.1 N NaOH
CAT, TFA
130° C.    a

Na¹²³I
in 0.1 N NaOH
Iodobead ®
TFA
130° C.    b

-continued
REACTION SCHEME 6

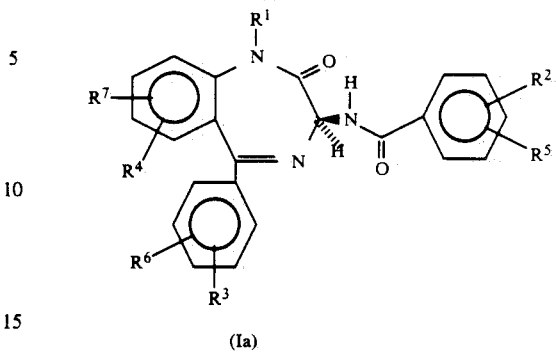

(Ia)

Amide derivatives (III) are prepared as described in Scheme 1 (following the procedures disclosed in U.S. Pat. No. 4,820,834, hereby incorporated by reference). 3(S)-Amino-1,3 dihydro-1-substituted-5-aryl-2H-1,4-benzodiazepine-2 ones containing various substitutents in the aryl rings (prepared as described in U.S. Pat. No. 4,820,834, in U.S. Pat. No. 4,628,084, hereby incorporated by reference) are reacted with an aryl acyl halide or anhydride containing various substituents on the aryl ring in the presence of an amine base, preferably triethylamine, in methylene chloride to give the amide derivatives (III), wherein X, Y and Z are, independently, hydrogen, iodo, or bromo, with the proviso that at least one of X, Y or Z is not hydrogen.

Similarly, as shown in Scheme 2, the 3(S)-amino-1,3-dihydro-1-substituted-5-aryl-2H-1,4-benzodiazepine-2-one may be reacted with an indole acyl halide in the presence of an amine base, preferably triethylamine, in methylene chloride to give the amide derivative (IV), wherein X,Y and Z are, independently, hydrogen, iodo or bromo, with the proviso that at least one of X, Y or Z is not hydrogen.

Urea derivatives (V) are prepared as described in Scheme 3 (following the procedures disclosed in U.S. Pat. No. 4,820,834). 3(S)-Amino-1,3-dihydro-1 substituted-5-aryl-2H-1,4-benzodiazepine-2-ones containing various substituents in the aryl rings (II) are reacted with an aryl isocyanate containing various substituents on the aryl ring to give the urea derivates (V), wherein X, Y and Z are, independently, hydrogen, iodo, or bromo, with the proviso such that at least one of X, Y or Z is not hydrogen.

Three routes have been developed for the synthesis of ¹²³I and ¹²⁵I labeled 3(S)-1,3-dihydro-3-aroylamino-1-substituted-5-aryl-2 H-1,4-benzodiazepin-2-ones (Ia) and (R)-N-(2,3-dihydro-1-substituted-2-oxo-5-aryl-1H 1,4-benzodiazepin-3-yl)-N'-(aryl)ureas (Ib). The first (shown in Scheme 4 and Scheme 5, for the amides and ureas, respectively) involves the replacement of ¹²⁷I by ¹²³I (or ¹²⁵I) via exchange. The amide (III) or urea (IV), wherein $X_a$, $Y_a$ and $Z_a$ are independently, hydrogen or iodo, such that at least one is not hydrogen, is heated at 150°-200° C., preferably 180°-190° C., with a sodium hydroxide solution of Na¹²³I (or Na¹²⁵I) in the presence of cupric sulfate and ammonium sulfate under a stream of air for 0.5 to 10 hours, preferably about 2 hours, to give the desired amide (Ia) or urea (Ib) bearing ¹²³I (or ¹²⁵I) in low specific activity (30-400 Ci/mmol).

The second route which involves exchange of ¹²³I (or ¹²⁵I) for ⁸⁰Br is also described in Scheme 4 and Scheme 5. The amide (III) or urea (V), wherein $X_a$, $Y_a$, and $Z_a$ are, independently, hydrogen or bromo, with the proviso that at least one of $X_a$, $Y_a$, and $Z_a$ is not hydrogen, are heated at 150°–200° C., preferably 180°–190° C., with a sodium hydroxide solution of $Na^{123}I$ (or $Na^{125}I$) in the presence of cupric sulfate and ammonium sulfate under a stream of air for 0.5 to 10 hours, preferably about 2 hours, to give the desired amide (Ia) or urea (Ib) bearing $^{123}I$ (or $^{125}I$) in high specific activity (approximately 2,000 Ci/mmol).

The third route (described in Scheme 6a and 6 b) involves radioiododestannylation of an appropriate tri-alkyl tin derivative with $Na^{123}I$ (or $Na^{125}I$). The amide (III) (or urea), wherein $X_b$ is tri-$C_1$-$C_5$-alkyl tin and $Y_b$ and $Z_b$ are hydrogen (prepared by the reaction of a 3(S)-amino-1,3-dihydro-1-substituted-5-aryl-2H-1,4-benzodiazepin-2 -one with the NHS ester of a (tri-$C_1$-$C_6$-alkyltin)benzoate), is reacted with a sodium hydroxide solution of $Na^{123}I$ (or $Na^{125}I$) in the presence of TFA and either chloramine-T (Scheme 6a) or an Iodobead ® (Scheme 6b) at 100–150° C., preferably about 130° C., for 15 minutes to 5 hours, preferably 1 hour, to give the desired amide (Ia) (or urea) bearing $^{123}I$ (or $^{125}I$) in high specific activity (2,000 Ci/mmol).

It is noted that salts of other radiohalogens (such as $Na^{122}I$, $Na^{131}I$, $Na^{75}Br$, $Na^{77}Br$, $Na^{82}Br$ or $Na^{211}At$) may be utilized to prepare appropriately labelled compounds of Formula I.

The following examples are given for the purpose of illustrating the present invention and shall not be construed as being limitations on the scope or spirit of the instant invention.

EXAMPLE 1

3(S)-1,3-Dihydro-3-(4-iodobenzoylamino)-1-methyl-5-phenyl-2H-1,4-benzodiazepin-2-one 3(S)-(-)3-Amino-1,3-dihydro-1-methyl-5-phenyl-2H-1,4-benzodiazepin-2-one (1.0 g, 3.77 mmol) (obtained as described in U.S. Pat. No. 4,820,834, issued Apr. 11, 1989 to Evans et al.) was dissolved in $CH_2Cl_2$ (15 ml) and treated with 4-iodobenzoyl chloride (1.02 g, 3.83 mmol) followed by triethylamine (0.38 g, 3.77 mmol). The mixture was stirred at room temperature for 30 minutes and concentrated in vacuo. The residue was chromatographed on silica gel (5% $Et_2O/CH_2Cl_2$) and the combined product fractions evaporated to dryness in vacuo. The $Et_2O$ (15 ml) was added and evaporated in vacuo three times. The residue was triturated with petroleum ether and evaporated to dryness in vacuo to give the title compound: (m p. 65°–50° C.).

TLC: Silica gel (5% $Et_2O/CH_2Cl_2$), $R_f=0.43$
NMR: Consistent with structure
HPLC: Greater than 99% pure
Mass Spectra: m/e=495 (M+)
Anal. Calcd. for $C_{23}H_{18}IN_3O_2 \cdot 0.1C_6H_{14}$: C, 56.24; H, 3.88; N, 8.34;
Found: C, 56.02; H, 3.69; N, 8.15.

EXAMPLE 2

[$^{123}I$]3(S)-1,3-Dihydro-3-(4-iodobenzoylamino)-1-methyl-5-phenyl-2 H-1,4-benzodiazepin-2-one from 3(S)-1,3-dihydro-3-(4-iodobenzoylamino)-1-methyl-5-phenyl-2H-1,4 benzodiazepin -2-one via Exchange ($^{123}I$ for $^{127}I$).

Into a 2 mL vial with a teflon septum screw cap was weighed 0.02 mg of 3(S)-1,3-dihydro-3 (4-iodobenzoylamino) -1-methyl-5-phenyl-2H-1,4-benzodiazepin-2-one, 0.3–0.5 mg of cupric sulfate, and 9.0–11.0 mg of ammonium sulfate. The $Na^{123}I$ (1–20 mCi) in 0.1N sodium hydroxide was quantitatively transferred from the commercial vial to the reaction vial via a microsyringe. The commercial vial was rinsed with 50 μl of acetonitrile and this rinse was added to the reaction vial to form a slurry of reactants. The sealed vial was attached to a nitrogen stream inlet and a charcoal trap outlet and was heated to dryness under nitrogen in a sand bath (150° C. for 15 minutes). The nitrogen inlet was then replaced with an air inlet and the reaction was heated under a gentle stream of air in a 180°–190° C. sand bath for 2 hours.

The vial was cooled and rinsed 4 times with 50 μl portions of ethanol. Each rinse was filtered through a 0.22 μm Acrodisc filter into a 5 dram vial. This filtrate was reduced in volume to a residue via rotary evaporation. The residue was then formulated into a fine emulsion as described in Example 7. HPLC analysis of the filtrate prior to evaporation showed that 95–99% of the radioactivity formed [$^{123}I$]3(S)-1,3-dihydro-3-(4-iodobenzoylamino)-1-methyl-5-phenyl -2H-1,4-benzodiazepin-2-one [which eluted at 11.7–11.9 minutes under an isocratic gradient, using 50% each of ethanol and water (0.1% $H_3PO_4$) at a flow rate of 1 ml/min]. Radiochemical yield was 35–75%.

EXAMPLE 3

[$^{123}I$]3(S)-1,3-Dihydro-3-(4-iodobenzoylamino)-1-methyl -5-phenyl-2H-1,4-benzodiazepin-2-one via Radioiododebromination of 3(S)-1,3-Dihydro-3-(4-bromobenzoylamino) -1 methyl-5-phenyl-2H-1,4-benzodiazepin-2-one Step A: Preparation of 3(S)-1,3-dihydro-3-(4-bromobenzoylamino)-1-methyl-5-phenyl-2 H-1,4-benzodiazepin-2-one The title compound was prepared from 3(S)-(-)-3-amino-1,3-dihydro-1-methyl-5-phenyl-2H-1,4 -benzodiazepin-2-one and 4-bromobenzoyl chloride utilizing the procedure of Example 1.

Step B: Radioiododebromination of 3(S)-1,3-dihydro-3-(4-bromobenzoylamino) -1-methyl-5-phenyl-2H-1,4-benzodiazepin-2-one Into a 2 ml vial with a teflon septum screw cap was weighed 0.10 mg of 3(S)-1,3-dihydro-3-(4-bromobenzoylamino) -1-methyl-5-phenyl-2H-1,4 benzodiazepin-2-one, 0.3 mg of cupric sulfate, and 9.0 mg of ammonium sulfate. The $Na^{123}I$ (1–20mCi) in 0.1 N sodium hydroxide was quantitatively transferred from the commercial vial to the reaction vial via a microsyringe. The commercial vial was rinsed with 50 μl of acetonitrile and this rinse was added to the reaction vial to form a slurry of reactants. The sealed vial was attached to a nitrogen stream inlet and a charcoal trap outlet. The contents were heated to dryness under nitrogen in a sand bath (150° C. for 15 minutes). The nitrogen inlet was then replaced with an air inlet and the reaction was heated under a gentle stream of air in a 180°–190° C. sand bath for 2 hours.

After cooling, the reaction vial was rinsed with 100 μl of ethanol. The HPLC isocratic elution system consisted of 37% ethanol in water (0.1% $H_3PO_4$), flowing at 1.0 ml/min. The product eluted from 71 to 86 minutes and the bromo starting material eluted from 55 to 66 minutes. The HPLC results indicated a 98.7% radiochemical purity. The radiochemical yield was 39.5%

The HPLC fraction of product was concentrated using a Waters C-18 Sep-pak cartridge. The cartridge was prepared with 10 ml of ethanol followed by a 10 ml rinse with water. The HPLC product fraction was applied to the cartridge which was then rinsed with 20 ml of water. The cartridge was then inverted and rinsed with several 0.5 ml fractions of ethanol. The majority of the radioactive product was collected in the second and third fractions.

EXAMPLE 4

[$^{123}$I]3(S)-1,3-Dihydro-3-(4-iodobenzoylamino)-1-methyl-5-phenyl-2 H-1,4 benzodiazepin-2-one via Radioiododestannylation of 3(S)-1,3-Dihydro-3-[4-(tri-n-butyltin) -benzoylamino]-1-methyl-5-phenyl-2H-1,4-benzodiazepin-2-one

Step A: Formation of the Free Base of 3(S)-(-)-Amino-1,3-dihydro-1-methyl-5-phenyl-2 H-1,4-benzodiazepin-2-one To 3(S)-(-)-amino-1,3-dihydro-1-methyl-5-phenyl-2H-1, 4-benzodiazepin-2-one camphor sulfonate salt was added 5 ml of 10% NaHCO$_3$ (w/v) and 10 ml of ethyl acetate. The phases were thoroughly mixed and separated. The aqueous phase was re extracted with two 10 ml portions of ethyl acetate. The organic layers containing the free amine were combined and washed with 3 ml of H$_2$O and 3 ml of brine. The organic phase was dried over anhydrous Na$_2$SO$_4$ and concentrated to dryness in vacuo. The amine was used immediately after drying.

Step B: Preparation of 3(S)-1,3-dihydro-3-[4-(tri-n-butyltin)-benzoylamino]-1-methyl-5-phenyl -2H-1,4-benzodiazepin-2-one To a 4 ml Wheaton vial with a teflon septum screw cap and magnetic stir bar was added 101.64 mg (0.20 mmol) of N-hydroxysuccinimidyl-4-(tri-n-butyltin) benzoate (NHS ester) (prepared by the method of Zalutsky, M.R. and Narula, A.S. *Appl. Radiat. Isot.,* 38(12):1051–1055, 1987). 3(S)-(-)-Amino-1,3-dihydro-1-methyl-5-phenyl-2H-1,4-benzodiazepin-2-one (0.25 mmol) was diluted with 3 ml of DMF. This solution was added to the NHS ester in the Wheaton vial. The pH of the solution was adjusted to 8 by dropwise addition of dry triethylamine. The sealed reaction was stirred at room temperature for 48 hours, maintaining the pH between 8-9 by addition of more triethylamine (approx. 0.10 ml was the total added). The reaction was monitored by analytical TLC (50% ethyl acetate/hexane on silica gel, product Rf=0.50). After 48 hours, the product (110 mg, 66.8% yield) was purified by prep TLC. NMR analysis was consistent with the structure.

Step C: Radioiododestannylation of 3(S)-1,3-Dihydro-3-[4-(tri-n-butyltin)-benzoylamino] -1-methyl-5-phenyl-2H-1,4-benzodiazepin-2-one

*Chloramine-T Oxidant Method* Into a 0.3 ml conical vial with a teflon septum screw cap was added 9.30 mg (14 μmol) of 3(S)-1,3-dihydro-3-[4-tri-n-butyltin) benzoylamino]1-methyl-5-phenyl-2H-1,4-benzodiazepin-2-one, 10.3 mg (45 μmol) of chloramine-T (CAT), 1.7 mCi of Na$^{123}$I in 0.1 N sodium hydroxide, a stir bar, and 100 μl of TFA. The vial was sealed and heated with stirring for 1 hour at 130° C. (sand bath). After cooling, analysis was performed by HPLC [43% ethanol in water (0.1% H$_3$PO$_4$), 1 ml/min]. The radioactive yield of product (which eluted at 25–26.5 min) was 16% with 40% of the activity remaining as unreacted Na$^{123}$I.

*Iodobead ® Oxidant Method* Into a 0.3 ml conical vial with a teflon septum screw cap was added 32.0 mg of 3(S)-1,3-dihydro-3-[4-(tri-n-butyltin)-benzoylamino] -1-methyl-5-phenyl-2H-1,4-benzodiazepin-2-one, an Iodobead ® (purchased from pierce), 2.44 mCi of Na$^{123}$I in 0.1 N sodium hydroxide, a stir bar, and 100 μl of TFA. The sealed reaction was stirred and heated at 130° C. (sand bath) for 1 hour. After cooling, HPLC analysis was performed. A radioactive peak representing 15% of the total radioactivity eluted at 26.5 minutes. Spiking an HPLC injection of reaction mixture with cold 3(S)-1,3-dihydro-3-(4-iodobenzoylamino)-1-methyl-5-phenyl-2H-1, 4-benzodiazepin-2-one confirmed that the peak was the desired product. A side product representing 49% of the radioactivity eluted at 6.5–7 minutes. Spiking an injection of the reaction mixture with cold 4-iodobenzoic acid showed that the exocyclic amide bond of the starting material had been hydrolyzed (to form [$^{123}$I]4-iodobenzoic acid which eluted at 6.7–7 minutes) in the strongly acidic TFA medium with prior or subsequent radioiododestannylation of the tin group.

EXAMPLE 5

[$^{123}$I]3(S)-1,3-Dihydro-3-(3-iodobenzoylamino)-1-methyl-5-phenyl-2H-1, 4-benzodiazepin-2-one

Step A: Preparation of 3(S)-1,3-Dihydro-3-(3-iodobenzoylamino) -1-methyl-5-phenyl-2H-1,4-benzodiazepin-2-one The title compound is prepared from 3(S)-(-)-3-amino-1, 3-dihydro-1-methyl-5-phenyl-2H-1,4-benzodiazepin-2-one and N-hydroxysuccinimidyl-3-iodobenzoate utilizing the procedure of Example 1.

Step B: [$^{123}$I]3(S)-1,3-Dihydro-3-(3-iodobenzoylamino) -1-methyl-5-phenyl-2H-1,4-benzodiazepin-2-one via Exchange ($^{123}$I For $^{127}$I)

The title compound is prepared from 3(S)-1,3-dihydro-3-(3-iodobenzoylamino)-1-methyl-5-phenyl-2H-1, 4 benzodiazepin-2-one utilizing the procedure of Example 2.

EXAMPLE 6

[$^{123}$I]3(S)-1,3 Dihydro-3-(3-iodobenzoylamino)-1-methyl-5-(2-fluorophenyl) -2H-1,4-benzodiazepin-2-one

Step A: Preparation of 3(S)-1,3-Dihydro-3-(3-iodobenzoylamino) -1 methyl-5-(2-fluorophenyl)-2H-1, 4-benzodiazepin-2-one The title compound is prepared from 3(S)-amino-1,3-dihydro-1-methyl-5-(2-fluorophenyl)-2H-1, 4-benzodiazepin-2-one and 3-iodobenzoyl chloride utilizing the procedure of Example 1.

Step B: [$^{123}$I]3(S)-1,3-Dihydro-3-(3-iodobenzoylamino) -1-methyl-5-(2-fluorophenyl)-2H-1,4-benzodiazepin-2-one via Exchange ($^{123}$I for $^{127}$I)

The title compound is prepared from 3(S)-1,3-dihydro-3-(3-iodobenzoylamino)-1-methyl-5-(2-fluorophenyl)-2H-1, 4-benzodiazepin-2-one utilizing the procedure of Example 2.

EXAMPLE 7

[$^{123}$I](R)-N-(2,3-Dihydro-1-methyl-2-oxo-5-phenyl-1H-1, 4-benzodiazepin-3-yl)-N'-(3-iodophenyl)urea

Step A: Preparation of (R)-N-(2,3-Dihydro-1-methyl-2-oxo-5-phenyl-1H-1, 4-benzodiazepin-3-yl)-N'-(3-bromophenyl)urea The title compound was prepared as described in U.S. Pat. No. 4,820,834.

Step B:
[$^{123}$I](R)-N-(2,3-Dihydro-1-methyl-2-oxo-5-phenyl-1H-1, 4-benzodiazepin-3-yl)-N'-(3-iodophenyl)urea via Radioiododebromination of (R)-N-(2,3-Dihydro-1-methyl-2-oxo-5-phenyl-1H-1, 4-benzodiazepin-3-yl)-N'-(3-bromophenyl)urea The title compound is prepared from (R)-N-(2,3-dihydro)-1-methyl-2-oxo-5-phenyl-1H-1,4-benzodiazepin-3-yl)-N'-(3-bromophenyl) urea utilizing the procedure of Example 3B.

EXAMPLE 8

Incorporation of [$^{123}$I]3(S)-1,3-dihydro-3-(4-iodobenzoylamino)-1-methyl-5-phenyl-2H-1,4-benzodiazepin-2-one into an IV Microfine Emulsion The IV microfine emulsion formulation consisted of 20% (w/w) oil plus compound and an 80% aqueous phase. The title compound of Example 2, in a 5 dram vial, was dissolved in the oil phase which was a 50/50 (w/w) soybean/safflower oil mixture. The aqueous phase contained L-α-phosphatidyl choline (99% pure), glycerin (USP), and water (sterile filtered, double distilled). After mixing the radiotracer with the oil phase, the aqueous phase was added and the two phases were thoroughly mixed until an aqueous dispersion was formed. This material was then processed into a fine emulsion in a microfluidizer (model no. 110-S, Microfluidics Corp.). The quantities of each component were selected to give the final composition of: oils and radiotracer (20.0%), L-α-phosphatidyl choline (1.25%), glycerin (2.0%), and water (76.75%).

EXAMPLE 9

Biochemical and Biological Studies

In Vitro Binding Assay

Saturation studies using either [$^3$H](R)-N-(2,3-dihydro-1-methyl-2-oxo-5-phenyl-1H-1, 4-benzodiazepin-3-yl)-1H-indole-2-carboxamide (86.8 Ci/mmol; obtained from New England Nuclear) or [$^{123}$I]3(S)-1,3-dihydro-3-(4-iodobenzoylamino)-1-methyl-5-phenyl-2H-1, 4-benzodiazepin-2-one were conducted utilizing the method of Chang, et al., *Mol. Pharmacol.*, 30:212–217, 1986. Pancreatae were removed from either rats or rabbits immediately after euthanasia and placed in ice-cold buffer (50 mM Tris·HCl (pH 7.4), 5 mM MgCl$_2$, 5 mM DTT, 2 mg/ml BSA and 0.14 mg/ml bacitracin). The tissue (0.5 g pancreas) was homogenized in 200 ml of the ice-cold Tris buffer. Aliquots (0.1 ml) were added to various concentrations of radioligand (5 ml) in Tris buffer, incubated for 60 min at ambient temperatures, and filtered over GC-filters. After washing with ice cold Tris buffer (2×5 ml), the filters were air dried and counted in 10 ml of liquid scintillation cocktail (PCS, Amersham) in a Beckman LSC-5000. Data were converted to Molar concentrations and analyzed via SCA-FIT, and data are presented by the method of Scatchard. The specific activity of the radioiodinated product was determined as that which provided the same concentration of receptor as obtained with the tritiated ligand.

In Vivo Distribution Necropsy

In rats or rabbits, 10 μCi of either [$^3$H](R)-N-(2,3-dihydro-1-methyl-2-oxo-5-phenyl-1H-1, 4-benzodiazepin-3-yl)-1H-indole-2-carboxamide or ][$^{123}$I]3(S)-1,3-dihydro-3-(4-iodobenzoylamino)-1-methyl-5-phenyl-2H-1, 4-benzodiazepin-2-one [in 50 mM PBS (pH 7.4) containing 20% EtOH and 1 % BSA] was administered intravenously via tail vein. Animals were euthanized at various times (15 min to 2 hr), and organs of interest removed for assay. Biopsy samples were counted in an autogamma counter (50% counting efficiency) for $^{123}$I labeled radioligand. For the tritiated radioligand, in rats and rabbits, 10 to 50 mg samples of pancreas and, in rats, several regions of CNS (cortex, interpeduncular nucleus, and substantial nigra) were solubilized in protosol ® (New England Nuclear). Liquid scintillation cocktail was added and the samples were dark adapted for 16 hours, then counted in a liquid scintillation counter with automatic quench correction. Results were the average of at least five animals and were expressed as % dose/g (wet weight).

Receptor-mediated binding was determined by diluting the specific activity of the radioligand by the addition of 0.4 mg/kg (R)-N-(2,3-dihydro-1-methyl-2-oxo-5-phenyl 1H-1,4-benzodiazepin-3-yl)-1H-indole-2-carboxamide. Additionally, for one study with [$^{123}$I3(S)-1,3-dihydro-3-(4-iodobenzoylamino)-1-methyl-5-phenyl-2H-1, 4-benzodiazepin-2-one, (R)-N-(2,3-dihydro-1-methyl-2-oxo-5-phenyl-1H-1,4-benzodiazepin-3-yl)-1H-indole-2 carboxamide (1 mg/kg) was intraperitoneally preinjected 15 min after injection of the radioligand.

Imaging

Rats under ketamine/acepromazine anesthesia were positioned for either anterior or posterior dynamic (128×128×16) images. A large-field-of-view gamma camera with a low energy, all purpose collimator, peaked for $^{123}$I, was utilized. Thirty one-minute images were acquired immediately post intravenous administration of 0.2 mCi of [$^{123}$I]3(S)-1,3-dihydro-3-(4-iodobenzoylamino)-1-methyl -5-phenyl-2H-1,4-benzodiazepin-2-one. To enable visualization of the liver alone, an unblocked rat was injected with 0.125 mCi of $^{99m}$Tc-albumin colloid. A static one-minute image (128×128×16) was obtained then, without moving the animal, the dose of [$^{123}$I]3(S)-1,3-dihydro-3-(4-iodobenzoylamino) -1-methyl-5-phenyl-2H-1,4-benzodiazepin-2-one was injected and imaging proceeded as described. Rabbits and African green monkeys under ketamine/xylazine anesthesia were positioned for an anterior view and imaged as the rats were after an intravenous injection of 0.5 mCi of [$^{123}$I] (S)-1,3-dihydro-3-(4-iodobenzoylamino) -1-methyl-5-phenyl-2H-1,4-benzodiazepin-2-one for rabbits, and 1.3 mCi for monkeys.

All blocked studies utilized a coinjection of 1 mg/kg of (R)-N-(2,3-dihydro-1-methyl-2-oxo-5-phenyl-1H-1, 4-benzodiazepin-3-yl)-1H-indole-2-carboxamide. Computer analysis was utilized to define the time course of distribution and to maximize the ability to visualize the pancreas. Where applicable, the $^{99m}$Tc-albumin colloid liver image was subtracted from the [$^{123}$I](S)-1,3-dihydro-3-(4-iodobenzoylamino) -1-methyl-5-phenyl-2H-

1,4-benzodiazepin-2-one images to further maximize visualization of the pancreas. Reduced data were expressed as count rates in regions of interest (ROI) as a function of time.

In Vitro Results

[$^{123}$I]3(S)-1,3-dihydro-3-(4-iodobenzoylamino)-1-methyl-5-phenyl-2H1, 4-benzodiazepin-2-one exhibits an affinity for the CCK-A receptor from rat pancreas which is 3-fold lower than that of [$^3$H](R)-N-(2,3 dihydro-1-methyl-2-oxo-5-phenyl-1H 11,4-benzodiazepin-3-yl)-1H-indole-2-carboxamide.

The concentration of CCK-A receptors in the pancreas was determined in rats and rabbits. The average concentration in rats ($R_o = 150 \pm 32$ pmol/g tissue) is 12-fold higher than that determined in the rabbit pancreas ($R_o = 12.3$ pmol/g tissue, average of two determinations). The affinity of [$^3$H]N-(2,3-dihydro-1-methyl-2-oxo-5-phenyl-1H-1, 4-benzodiazepin-3-yl)-1H-indole-2-carboxomide for the CCK-A receptor from rabbit pancreas does not differ from that determined using rat pancreas CCK-A receptor.

In Vivo Results

The time course of [$^{123}$I]3(S)-1,3-dihydro-(4-iodobenzoylamino)-1-methyl-5-phenyl-2H-1, 4-benzodiazepin-2-one localization in the pancreas of rats is provided in Table 2. Coinjection of (R)-N-(2,3-dihydro-1-methyl-2-oxo-5-phenyl-1H-1,4-benzodiazepin-3-yl) -1H-indole-2-carboxamide provided 60-70% reduction of localization (Table 3).

TABLE 2

Distribution of [$^{123}$I]3(S)-1,3-dihydro-3-(4-iodobenzoylamino)-1-methyl-5-phenyl-2H-f,4-benzodiazepin-2-one in rat pancreas following i.v. injection (error range at 95% confidence intervals):

| TIME (min.) | % DOSE/GRAM |
|---|---|
| 15 | 2.07 ± 0.46 |
| 30 | 1.90 ± 0.71 |
| 60 | 1.14 ± 0.13 |

TABLE 3

Distribution of [$^{123}$I]3(S)-1,3-dihydro-3-(4-iodobenzoylamino)-1-methyl-5-phenyl-2H-1,4-benzodiazepin-2-one in rat pancreas following i.v. coinjection with 0.4 mg/kg) (R)-N-(2,3-dihydro-1-methyl-2-oxo-5-phenyl-1H-1,4-benzodiazepin-3-yl)-1H-indole-2-carboxamide (error range at 95% confidence intervals.)

| TIME (min.) | % DOSE/GRAM |
|---|---|
| 15 | 0.574 ± 0.065 |
| 30 | 0.727 ± 0.18 |
| 60 | 0.472 ± 0.085 |

The distribution of [$^{123}$I]3(S)-1,3-dihydro-3-(4-iodobenzoylamino)-1-methyl-5-phenyl-2H -1,4-benzodiazepin-2-one at 30 minutes post-injection in various regions of interest is presented in Table 4 and Table 5.

TABLE 4

Biodistribution [$^{123}$I]3(S)-1,3-dihydro-3-(4-iodobenzolamino)-1-methyl-5-phenyl-2H-1,4-benzodiazepin-2-one in rats at 30 minutes post-i.v. injection of 10 μ Ci (error range at 95% confidence intervals):

| ORGAN | % DOSE/GRAM |
|---|---|
| Blood | 0.307 ± 0.051 |

TABLE 4-continued

Biodistribution [$^{123}$I]3(S)-1,3-dihydro-3-(4-iodobenzolamino)-1-methyl-5-phenyl-2H-1,4-benzodiazepin-2-one in rats at 30 minutes post-i.v. injection of 10 μ Ci (error range at 95% confidence intervals):

| ORGAN | % DOSE/GRAM |
|---|---|
| Muscle | 0.319 ± 0.086 |
| Pancreas | 2.54 ± 0.93 |
| Liver | 1.96 ± 0.56 |
| P. Sphincter | 1.25 ± 0.33 |
| Transverse Colon | 0.50 ± 0.18 |
| Descending Colon | 0.418 ± 0.073 |
| Sigmoidal Colon | 0.500 ± 0.13 |

TABLE 5

Biodistribution of [$^{123}$I]3(S)-1,3-dihydro-3-(4-iodobenzoylamino)-1-methyl-5-phenyl-2H-1,4-benzodiazepin-2-one in rats at 30 minutes post-i.v. coinjection of 10 μCi with 0.4 mg/kg (R)-N-(2,3-dihydro-1-methyl-2-oxo-5-phenyl-1H-1,4-benzodiazepin-3-yl)-1H-indole-2-carboxamide (error range at 95% confidence intervals):

| ORGAN | % DOSE/GRAM |
|---|---|
| Blood | 0.236 ± 0.03 |
| Muscle | 0.271 ± 0.04 |
| Pancreas | 0.900 ± 0.22 |
| Liver | 1.69 ± 0.39 |
| P. Sphincter | 0.705 ± 0.19 |
| Transverse Colon | 0.384 ± 0.06 |
| Descending Colon | 0.434 ± 0.12 |
| Sigmoidal Colon | 0.600 ± 0.47 |

In addition to the pancreas, specific localization is obtained in the region of the pyloric sphincter. Although consistently higher localizatiOn is obtained in the duodenum and colon, significant blockade of localization was not demonstrated. The ratio of activity in the pancreas to that in the blood and liver suggests sufficient localization to provide in vivo images of the pancreas. With [$^3$H](R)-N-(2,3-dihydro-1-methyl-2-oxo-5-phenyl-1H-1, 4-benzodiazepin-3-yl)-1H-indole-2-carboxamide, 2.1% dose/g localized in the pancreas, of which 90% was receptor-mediated (0.25% dose/g when co-injected with 1 mg/kg carrier (R)-N-(2.3-dihydro-1-methyl-2-oxo-5-phenyl-1H-1, 4,-benzodiazepin-3-yl)-1H-indole-2-carboxamide).

Images of the distribution of [$^{123}$I]3(S)-1,3-dihydro-3-(4-iodobenzoylamino)-1-methyl -5-phenyl-2H-1,4-benzodiazepin-2-one were obtained in rats for 30 min following intravenous injection. Radioactivity in biopsied samples was also determined in an autogamma counter and a dose calibrator. These results demonstrated that ]$^{123}$I3(S)-1,3-dihydro-3-(4-iodobenzoylamino)-1-methyl-5-phenyl-2H-1,4-benzodiazepin-2-one did localize in the pancreas by a receptor-mediated mechanism. Results were not different from those present in Tables 4 and 5.

While the foregoing specification teaches the principles of the present invention, with examples provided for the purpose of illustration, it will be understood that the practice of the invention encompasses all of the usual variations, adaptations, modifications, deletions, or additions of procedure and protocols described herein, as come within the scope of the following claims and its equivalents.

What is claimed is:

1. A compound of Formula I:

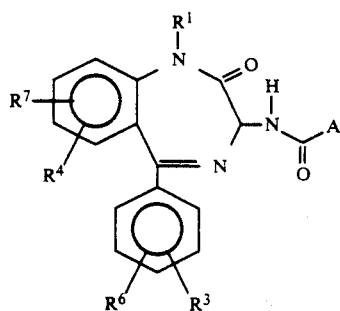

wherein:
A is

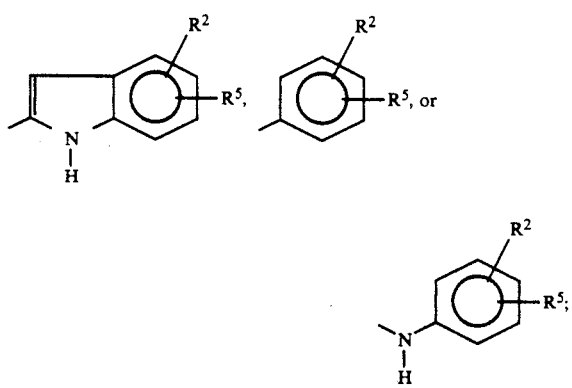

$R^1$ is H, $C_1$-$C_6$ linear or branched alkyl, $(CH_2)_nCOOR^8$, $(CH_2)_nOH$, $(CH_2)_nCN$, $(CH_2)_nNR^9R^{10}$,

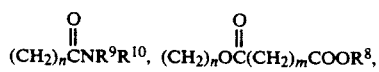

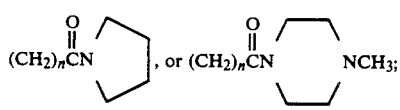

$R^2$ is H, —OH, —$NO_2$, F, Cl, $SO_3H$, loweralkyl, loweralkoxy, $(CH_2)_pCOOR^8$ or $(CH_2)_pNR^9R^{10}$;
$R^3$ is H, —OH, —$NO_2$, $CF_3$, F, Cl, loweralkyl, or loweralkoxy;
$R^4$ is H, —OH, —$NO_2$, $CF_3$, CN, F, Cl, loweralkyl, loweralkoxy, $(CH_2)_pCOOR^8$ or $(CH_2)_pNR^9R^{10}$;
$R^5$, $R^6$ and $R^7$ are, independently, H or a radionuclide selected from the group consisting of $^{122}I$, $^{123}I$, $^{125}I$, $^{131}I$, $^{75}Br$, $^{77}Br$, $^{82}Br$, $^{211}At$, with the proviso that at least one of $R^5$, $R^6$ and $R^7$ is not H;
$R^8$ is H or loweralkyl;
$R^9$ and $R^{10}$ are, independently, H or loweralkyl;
n is 1–4;
m is 1–2;
p is 0–4;
or pharmaceutically acceptable salt thereof.

2. A compound of claim 1 wherein:
A is

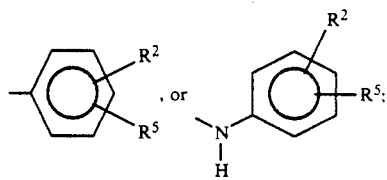

$R^1$ is $CH_3$;
$R^5$ is $^{123}I$, $^{125}I$ or $^{131}I$;
$R^2$, $R^3$, $R^4$, $R^6$ and $R^7$ are H;
or pharmaceutically acceptable salt thereof.

3. The compound of claim 1 which is [$^{123}I$]3(S)-1,3-dihydro-3-(4-iodobenzoylamino)-1-methyl-5-phenyl-2H-1, 4-benzodiazepin-2-one.

4. The compound of claim 1 which is [123I] 3(S)-1,3-dihydro-3-(4-iodobenzoylamino)-1-methyl-5-(2-fluorophenyl)-2H-1, 4-benzodiazepin-2-one.

5. The compound of claim 1 which is [$^{123}I$](R)-N-(2,3-dihydro-1-methyl-2-oxo-5-phenyl-1H-1, 4 benzodiazepin-3-yl)-N'-(3-iodophenyl)urea.

6. A method of diagonistic imaging of tissues bearing cholecystokinin-A receptors in a mammalian species which comprises administering to a mammalian species in need of such diagnostic imaging an effective amount of a compound of claim 1.

7. A method of diagnostic imaging of tissues bearing cholecystokinin-A receptors in a human which comprises administering to a human in need of such diagnostic imaging an effective amount of a compound of claim 1.

8. A method of diagnostic imaging of the pancreas and gallbladder in humans which comprises administering to a human in need of such diagnostic imaging an effective amount of a compound of claim 1.

9. A method of diagnostic imaging of the pancreas and gallbladder in humans which comprises the intravenous administration to a human in need of such diagnostic imaging an effective amount of a compound of claim 1.

10. A method of evaluation of disorders of the gastrointestinal tract in humans which comprises administering to a human in need of such evaluation an effective amount of a compound of claim 1.

11. A method of evaluation of disorders of the gastrointestinal tract in humans which comprises administering orally to a human in need of such evaluation an effective amount of a compound of claim 1.

12. A method of detection and quantification of cholecystokinin-A receptors in mammalian tissue which comprises the administering to a mammal in which such quantification is desired an effective amount of a compound of claim 1.

13. A method of treatment of pancreatic cancer in humans which comprises administering to a human in need of such treatment an effective amount of a compound of claim 1.

14. A method of treatment of gallbladder cancer in humans which comprises administering to a human in need such treatment an effective amount of a compound of claim 1.

* * * * *